US005733545A

United States Patent [19]
Hood, III

[11] Patent Number: 5,733,545
[45] Date of Patent: Mar. 31, 1998

[54] PLATELET GLUE WOUND SEALANT

[75] Inventor: Andrew G. Hood, III, Redwood City, Calif.

[73] Assignee: Quantic Biomedical Partners, Redwood City, Calif.

[21] Appl. No.: 607,515

[22] Filed: Feb. 27, 1996

Related U.S. Application Data

[63] Continuation-in-part of Ser. No. 398,022, Mar. 3, 1995, abandoned.

[51] Int. Cl.⁶ ........................................ A01N 63/00
[52] U.S. Cl. ............... 424/93.72; 424/94.1; 424/94.64; 424/530; 424/532; 424/534; 424/529; 530/382
[58] Field of Search ........................ 424/94.1, 93.72, 424/94.64, 530, 532, 534, 529; 530/382

[56] References Cited

U.S. PATENT DOCUMENTS

| | | | |
|---|---|---|---|
| 4,004,975 | 1/1977 | Lionetti et al. | 195/1.8 |
| 4,159,896 | 7/1979 | Levine et al. | 23/230 |
| 4,343,793 | 8/1982 | Wissler | 424/101 |
| 4,359,049 | 11/1982 | Redl et al. | 128/218 PA |
| 4,362,567 | 12/1982 | Schwarz et al. | 106/157 |
| 4,427,650 | 1/1984 | Stroetmann | 424/46 |
| 4,627,879 | 12/1986 | Rose et al. | 106/124 |
| 4,631,055 | 12/1986 | Redl | 604/82 |
| 4,735,616 | 4/1988 | Eibl et al. | 604/191 |
| 4,902,281 | 2/1990 | Avoy | 604/191 |
| 4,978,336 | 12/1990 | Capozzi et al. | 604/82 |
| 5,039,401 | 8/1991 | Columbus et al. | 210/117 |
| 5,165,938 | 11/1992 | Knighton | 424/532 |
| 5,185,001 | 2/1993 | Galanakis | 604/5 |
| 5,290,552 | 3/1994 | Sierra et al. | 424/94.64 |
| 5,304,372 | 4/1994 | Michalski et al. | 424/94.64 |
| 5,318,782 | 6/1994 | Weis-Fogh | 424/529 |
| 5,330,974 | 7/1994 | Pines et al. | 514/21 |
| 5,405,607 | 4/1995 | Epstein | 424/94.64 |
| 5,428,008 | 6/1995 | Chao et al. | 514/8 |
| 5,437,598 | 8/1995 | Antwiler | 494/1 |
| 5,585,007 | 12/1996 | Antanavich | 210/782 |

FOREIGN PATENT DOCUMENTS

| | | |
|---|---|---|
| A 0 068 047 | 1/1983 | European Pat. Off. |
| A 0 068 048 | 1/1983 | European Pat. Off. |
| A 0 446 713 | 9/1991 | European Pat. Off. |
| WO 86/03122 | 6/1986 | WIPO |
| WO 88/02259 | 4/1988 | WIPO |
| WO 91/00046 | 1/1991 | WIPO |
| WO 91/09573 | 7/1991 | WIPO |

OTHER PUBLICATIONS

Bertolini, Francesco et al., "Platelet Concentrates Stored in Synthetic Medium after Filtration", *Vox Sang* 62:82–86 (1992).
Bloom, A. L., "Physiology of Blood Coagulation", *Haemostasis* 20:14–29 (1990).
Boyd, Robert F. et al., *Basic Medical Microbiology*, Little Brown and Company Third Edition 324–325 (1986).
Haemonetics Corporation product brochure entitled "Autologous Fibrin Gel".

Hartman, A.R. et al., "Autologous Whole Plasma Fibrin Gel; Intraoperative Procurement," *Arch. Surg.* 127:357–359 (1992) Mar.
Hill, A.G. et al., "Perioperative Autologous Sequestration II: A Differential Centrifugation Technique for Autologous Component Therapy: Methods and Results," *Proc. Am. Acad. Cardiovasc. Perf.* 14:122–125 (1993).
Hjortdal, Vibeke E. et al., "Vernous Ischemia in Skin Flaps: Microcirculatory Intravascular Thrombosis", *Plastic and Reconstructive Surgery* 93:366–374 (1994).
Hood, A.G. et al., "Perioperative Autologous Sequestration III: A New Physiologic Glue with Wound Healing Properties," *Trans. Am. Acad. Cardiovasc. Perf.* 14:126–129 (1993).
Hood, A.G. et al., "Autologous Platelet Gel: An Effective, Convenient, Bioactive Wound Sealant," Poster Session, Fibrin Sealant: Characteristics and Clinical Uses Conference, Bethesda, Maryland, Dec. 1994.
Hood, A.G., "Perioperative Blood Component Pheresis for Hemostasis and Wound Management: Mechanisms, Methods and Results," *Trans. Mech. Perf.* X, May 1995.
Keating, R.F. et al., "Tethered Cord Dural Repair With Intraoperative Autologous Fibrin Glue," Presented at American Assn. of Neurological Surgeons Pediatric Session, Vancouver, Canada, Dec. 1992 pp. 2–6.
Koerner, K. et al., "Quality of pooled platelet concentrates prepared from buffy coats and stored in an additive solution after filtration", *Ann Hematol.* 70:97–102 (1995).
Moretz, W.H., Jr. et al., "A simple autologous fibrinogen glue for otologic surgery," *Otolaryngology Head and Neck Surg.* 95:122–124 (1986).
Oz, M.C. et al., "Autologous Fibrin Glue From Intraoperatively Collected Platelet-Rich Plasma," *Ann. Thorac. Surg.* 53:530–531 (1992).
Quigley, R.L. et al., "Intraoperative Procurement of Autologous Fibrin Glue," *Ann. Thorac. Surg.* 56:387–389 (1993).
Reeder, G.D. et al., "Perioperative Autologous Sequestration I: Physiology, Phenomena and Art," *Proc. Am. Acad. Cardiovasc. Perf.* 14:118–121 (1993).

(List continued on next page.)

*Primary Examiner*—Chhaya D. Sayala
*Attorney, Agent, or Firm*—Skjerven, Morrill, MacPherson, Franklin & Friel LLP; Laura Terlizzi

[57] ABSTRACT

A plasma-buffy coat concentrate that comprises plasma, platelets at a concentration of at least $1.0 \times 10^9$ cells/ml, and fibrinogen at concentration of at least 5 mg/ml is described. The plasma-buffy coat concentrate can be combined with a fibrinogen activator to form a platelet glue wound sealant. A method for processing blood to produce the plasma-buffy coat concentrate is also provided. The method comprises centrifuging anticoagulated blood to remove red blood cells and produce a plasma-buffy coat mixture. Water is removed from the mixture to produce the plasma-buffy coat concentrate. A fibrinogen activator is mixed with the plasma-buffy coat concentrate to produce a wound sealant, which can then be applied to a wound to facilitate sealing and healing of the wound.

19 Claims, No Drawings

OTHER PUBLICATIONS

Reeder, G.D. et al., "Autologous Platelet Gel: An Autologous Method for Improved Wound Closure and Accelerated Healing," Poster Session, Fibrin Sealant: Characteristics and Clinical Uses Conference, Bethesda, Maryland, Dec. 1994 p. 68.

Sierra, D.H. et al., "Fibrin Sealant Adhesive Systems: A Review of Their Chemistry, Material Properties and Clinical Applications," *J. Biomat. App.* 7:309–352 (1993).

Silver, Frederick H. et al., "Preparation and use of fibrin glue in surgery", *Biomaterials* 16:891–903 (1995), Apr.

PLATELET GLUE WOUND SEALANT

CROSS-REFERENCE TO RELATED APPLICATIONS

This application is a continuation-in-part of U.S. patent application Ser. No. 08/398,022, filed Mar. 3, 1995, abandoned.

BACKGROUND OF THE INVENTION

1. Field of the Invention

This invention relates generally to wound sealants and in particular to a platelet glue wound sealant that is capable of enhancing healing of wounds.

2. Prior Art

The repair of damaged tissues and vessels is of universal concern to all surgical specialties. Damage to tissue, often as the result of the surgical procedure, can be difficult to repair. Continued fluid extravasation from or into a wound can result in increased patient morbidity, prolonged recovery, and the defeat of an otherwise promising outcome.

Following trauma or surgery, the normal healing process is diminished, a difficulty which can be exacerbated in the face of concomitant disease processes such as diabetes, which further impede the progress of healing. Serious fluid exudate from cut tissue surfaces can slow the healing of wounds, and serves as a culture medium for infection. In many tissues, fluid leaks occur regardless of how meticulous the surgical technique. Highly vascular tissue continues to bleed, even through the eschar of electrocautery, and continues to produce exudate for long periods after blood loss ceases.

Grafts in the arterial vascular tree, whether biological or synthetic, often leak at the suture line or through the graft material itself. Preexisting or iatrogenic coagulopathies frequently worsen this process. Wounds to the dura are notoriously difficult to repair, and historical approaches have reported failure rates with persistent cerebrospinal fluid leaks as high as 35% for some types of procedures. Persistent air leaks from resected lung tissue are difficult to repair and can result in a substantially extended recovery.

A multiplicity of approaches have been taken to address these problems. Although widely used, topical hemostats made from synthetic or highly modified biological materials are of limited effectiveness as sealants, ineffective as bonding agents, and result in a foreign body inflammatory response that in itself can prolong the healing process.

Fibrin glue, formed by cleaving fibrinogen with thrombin and polymerization of the resulting fibrin, has been widely proposed as a general solution to these problems and has even been termed the perfect operative sealant. Myriad attempts have been made to provide fibrin glue to the surgeon on demand. Fractionation of concentrated fibrinogen along with other clotting proteins from plasma by cold precipitation and density separation has been widely studied. Cryoprecipitation selectively extracts the components of the clotting cascade while discarding the majority of plasma protein and the bulk of the liquid volume. The typical yield from 450 ml of blood is 10 to 12 ml.

While widely used in Europe, commercially prepared pooled donor cryoprecipitate as a substrate for fibrin glue has not been available in the United States of America for many years due to regulatory agency fears of potential contamination and disease transmission. Single donor cryoprecipitate is not free from the danger of disease transmission, and HIV infection as the result of the topical application of fibrin glue from single donor derived cryoprecipitate has been documented. Autologous pre-donation of blood or plasma for the creation of autologous cryoprecipitate not only requires anticipation of the need, but also an ambulatory, motivated patient able to meet strict blood bank donation criteria coupled with the geographic availability of a qualified processing facility.

In the face of these obstacles, numerous approaches have been devised to facilitate the availability of single donor and autologous fibrinogen concentrates. While the products of these efforts have proven beneficial in a wide array of surgical applications, they all suffer from either complicated or prolonged processing techniques, high cost, the need for pre-donation, or a combination of such limitations. Additionally, tissue adhesive sealants based primarily on fibrinogen for function have been shown to impair healing rates due to the high fibrinogen content required for their effectiveness. However, fibrinogen concentrations less than 15 mg/ml have not been seen to inhibit wound healing, but rather have been shown to promote the early stages of wound healing.

There have recently been attempts to use autologous plasma, separated from whole blood by density difference either by gravity or centrifugation, as the substrate for a surgical topical tissue sealant upon activation of entrained fibrinogen by thrombin in the presence of ionic calcium. These methods result in a plasma product containing native levels of fibrinogen, which alone has been shown to be insufficient to reliably form a suitable fibrin gel. The strength of fibrin gels is directly related to the fibrinogen concentration, and naturally occurring levels are marginal at best for forming tissue sealants and adhesives. Below normal levels are often encountered due to disease, dilution by the anticoagulant solution required for collection, hemodilution coincident to the operative procedure itself, or a combination of such factors, yielding fibrin gels with less than acceptable mechanical and adhesive properties.

All fibrinogen-based sealant adhesives depend for their function on that portion of the coagulation cascade known as the common pathway, through conversion of fibrinogen to fibrin monomer, and thence its polymerization and cross-linking to form a stable mesh. The initiation of this process is most commonly by admixture of commercially obtained concentrated thrombin in aqueous solution containing ionized calcium. It is commonly held that in order to obtain a suitably functional and effective fibrin sealant adhesive, it is necessary to include a small concentration of dissolved calcium salts with the thrombin activator to provide ionic calcium. The requisite concentration of dissolved calcium varies from as little as 0.0036 to as much as 0.072 mg Ca++ per unit of thrombin. The addition of ionic calcium to thrombin results in higher cost, additional preparation steps, and increased complexity.

The presence of ionic calcium in a coagulum concurrently with platelets, however, allows the activated platelets to contract and extrude serous fluid from the coagulum, reducing its size by a substantial proportion and diminishing its adhesive and sealant properties. Thus, platelets have been rigorously eliminated from most fibrin glue preparations, or where present have been generally limited to less than physiologic concentration. The higher the platelet content, the greater likelihood of the addition of ionic calcium resulting in undesirable clot retraction.

Raised concentrations of platelets, however, have been shown to be of value in accelerating wound healing. Platelet-based wound healing extracts are decoctions of defibrinated plasma which are devoid of coagulation capability. Use of these preparations requires the addition of a carrier, such as microcrystalline collagen, to increase viscosity and mechanical integrity sufficiently for directed application. These carriers can in themselves result in a foreign body inflammatory response and thus inhibit or obviate any wound healing benefits.

It can therefore be seen that known methods and techniques for enhancing wound sealing and promoting wound healing fall short of providing a reliable, biocompatible, therapeutically effective composition. Exogenous materials induce inflammatory foreign body responses which delay or inhibit healing. Homologous products carry risk of disease transmission or bioincompatibility reactions. Highly concentrated fibrinogen solutions are time consuming to prepare and intrinsically inhibit wound healing. Whole plasma substrates often have fibrinogen levels too low for effective use, including those which incorporate platelets as augmentation, and rarely contain platelets at levels considered to be valuable in the acceleration of wound healing. Extracts of platelet concentrates, while seen to be effective as accelerants of wound healing, are not themselves capable of acting as wound sealants or adhesives.

Accordingly, there remains a need for an effective wound sealant which is safe, easily and quickly prepared, and which preferably augments or accelerates the healing process.

SUMMARY OF THE INVENTION

The present invention provides a plasma-buffy coat concentrate that comprises plasma, platelets at a concentration of at least $1.30 \times 10^9$ cells/ml, and fibrinogen at concentration of at least 5 mg/ml. When the plasma-buffy coat concentrate is combined with a fibrinogen activator in a concentration sufficient to initiate clot formation, a platelet glue wound sealant is formed. In a preferred embodiment, the wound sealant contains white cells at a concentration of at least $3.0 \times 10^7$ cells/ml and can be used to reduce or treat infection and promote wound healing in conjunction with platelets.

A method for processing blood to produce the plasma-buffy coat concentrate is also provided. The method comprises centrifuging anticoagulated blood to remove red blood cells and produce a plasma-buffy coat mixture. Water is removed from the mixture to produce the plasma-buffy coat concentrate. As described previously, a fibrinogen activator is mixed with the plasma-buffy coat concentrate to produce a wound sealant, which can then be applied to a wound to facilitate sealing and healing of the wound.

This wound sealant preparation method is readily performed peri-operatively with the patient's own blood. The method and compositions of this invention are useful for mammals, generally, and find particular use in humans.

DETAILED DESCRIPTION

The present invention provides a plasma-buffy coat concentrate that includes plasma and concentrated platelets and fibrinogen. In a preferred embodiment, the plasma-buffy coat concentrate also includes concentrated white cells. The plasma-buffy coat concentrate can be combined with a fibrinogen activator to produce a wound sealant.

The present invention also provides a method for processing blood that produces a plasma-buffy coat concentrate of this invention and can be used to prepare a platelet glue wound sealant that can promote wound sealing and wound healing. The method comprises centrifuging anticoagulated blood to remove red blood cells and produce a plasma-buffy coat mixture. Water is removed from the plasma-buffy coat mixture to produce a plasma-buffy coat concentrate. The concentrate is mixed with a fibrinogen activator to produce a wound sealant that, upon contact with damaged tissue seals the wound and can promote wound healing. The method can be performed peri-operatively to prepare an autologous platelet glue wound sealant.

The plasma-buffy coat concentrate and platelet glue wound sealant of this invention are described in detail below. Methods for preparing the compositions of this invention are described in detail hereinafter.

The Plasma-Buffy Coat Concentrate/Platelet Glue Wound Sealant

The plasma-buffy coat concentrate of this invention comprises plasma that contains platelets at a concentration of at least $1.0 \times 10^9$ cells/ml and fibrinogen at concentration of at least 5 mg/ml. Preferably, the platelet concentration is from about $1.0 \times 10^9$ cells/ml to about $2.5 \times 10^9$ cells/ml. In a preferred embodiment, the fibrinogen concentration is from about 5 to about 15 mg/ml.

The plasma-buffy coat concentrate can additionally include white cells, preferably at a concentration of at least $3.0 \times 10^7$ cells/ml. More preferably, the white cell concentration is from about $3.0 \times 10^7$ cells/ml to about $6.0 \times 10^7$ cells/ml. In a preferred embodiment, white cells present in the plasma-buffy coat concentrate comprise about 60 to about 70% lymphocytes, about 15 to about 25% monocytes, and about 5 to about 25% neutrophils.

A platelet glue wound sealant of this invention comprises the plasma-buffy coat concentrate described above and a fibrinogen activator in a concentration sufficient to initiate clot formation. Fibrinogen activators are well known and include, for example, thrombin and batroxobin. The fibrinogen activator can be present in various concentrations depending on the desired time to form a clot. When the fibrinogen activator is thrombin, at thrombin concentrations greater than 100 units per ml or so in the wound sealant, the fibrinogen concentration becomes the rate limiting step in coagulation. Higher concentrations of thrombin can be employed, but no additional benefit accrues. Furthermore, the danger of thrombin entering the intravascular space is greater. At concentrations lower than about 100 U/ml, the thrombin level is the rate controlling substance in the wound sealant. Thus, thrombin concentration can be used to control the time to gelation. The relationship of thrombin concentration to coagulation time is discussed in the methods section, hereinafter.

Although generally the fibrinogen activator is added exogenously, thrombin can be produced in the plasma-buffy coat concentrate from endogenous prothrombin present in the plasma component of the plasma-buffy coat concentrate. The citrate anticoagulant in the concentrate binds ionic calcium which is required to facilitate the coagulation cascade to cleave prothrombin and produce thrombin. Therefore, to produce thrombin from prothrombin present in the plasma-buffy coat concentrate, calcium is added in an amount sufficient to facilitate progression of the coagulation cascade.

Conveniently, calcium salts, such as, for example, 10% calcium chloride which is commercially available as a sterile pharmaceutical solution, are used. The amount of calcium salt required to sufficiently recalcify the plasma-buffy coat concentrate to facilitate production of endogenous thrombin for clot formation varies depending on the amount of residual citrate anticoagulant present in the preparation. However, addition of one part of 10% calcium citrate or equivalent calcium from anther source to 11 to 12 parts of plasma-buffy coat concentrate is sufficient. Use of calcium for activation of thrombin in the plasma-buffy coat concentrate is advantageous in procedures where a clotting time greater than one to two minutes is desired. Such clot formation times may be useful in bone defect procedures wherein bone or a bone growth matrix is added to the preparation prior to gelation of the clot.

The blood donor for the platelet glue wound sealant of this invention is preferably from the same species as the damaged tissue to which the wound sealant is applied. The wound sealant is useful for mammals generally, but is preferably used for humans. Preferably, donor and recipient are matched as in standard blood donations practices for the species involved. When possible, the blood donor is preferably the same animal to which the wound sealant is applied. When possible, preferably, the wound sealant is prepared either peri-operatively or just prior to application.

The fibrin coagulation process and platelet function are common to all mammalian species. Clearly, however, the closer the relationship between donor and recipient of the platelet glue wound sealant of this invention, the better for the recipient in terms of risk:benefit ratio and the likelihood of a desirable outcome. The wound sealant of this invention is particularly suitable for autologous applications, since it is capable of yielding substantial volumes of an effective agent in under thirty minutes, and thus is able to obviate the risks and complications associated with allogeneic blood product infusions.

Use of the Platelet Glue Wound Sealant

Although the wound sealant composition of this invention is particularly suited for human use, it is suitable for mammalian species, generally. In horses, for instance, wounds to the leg, particularly full thickness skin abrasions, are notoriously difficult to heal. Application of the platelet bearing wound sealant accelerates healing of wounds of this type, compared to conventional treatments.

Allogeneic use may be dictated where the blood volume of the recipient is insufficient to allow even temporary withdrawal of the blood volume needed for processing into a plasma-buffy coat mixture. In cardiac surgery for infants, for instance, the use of fibrinogen glues has been seen to be of substantial value, but the infants themselves are too small to provide their own blood for processing. The volume of such prior art glues required, however, often exceeded that which can be derived from a single donor, considerably increasing the risk of complications. By use of the wound sealant of this invention, however, a single unit of directed donor whole blood can be processed for use as a wound sealant. While the red cells are used to prime the pump, and the plasma is used for post-surgical coagulation factor correction, the plasma-buffy coat mixture can be used to prepare an effective topical adhesive sealant, substantially reducing post-operative blood loss without increasing the number of donor exposures.

A wide range of beneficial human uses has been explored and documented, in addition to those cited above. A series of compassionate use autologous applications have been performed, with a high degree of success and no complications. The platelet glue wound sealant of this invention has been used to seal leaks of cerebrospinal fluid through cut dura; to seal anastomoses of native and prosthetic vascular grafts; in operations with extensive incisions, such as radical prostatectomy, tram flap reconstructive surgery, radical necks, etc.; in plastic surgery including burn grafting and other free skin graft applications; and in highly vascular cut tissue, such as the kidneys, liver and spleen. The wound sealant of this invention has been uniformly effective in eliminating or greatly reducing post-operative bleeding and extravasation or loss of serous or other fluid in these applications.

Mixed with bone dust, the wound sealant of this invention has been demonstrated to provide rapid and uniform regrowth of bone in craniofacial and orthopedic procedures. Healing has also been dramatically accelerated in diabetic non-healing wounds, achieving successful closures where weeks of conventional therapies had failed. The wound sealant of this invention has also been successful in healing of septic wounds of longstanding resistance to standard approaches, including antibiotic-resistant bacterial infections.

When the wound sealant of this invention was applied to the sinus cavities following endoscopic sinus surgery, the regrowth of mucosa has been seen to be more rapid and uniform than with conventional treatment methods. Inner ear surgery has also been fruitful, successfully attaching prosthetic bones from the cochlea to the eardrum, and even for reconstruction of the eardrum itself. A few milliliters of wound sealant was allowed to gel in a medicine cup, transferred to an absorbent pad and compressed to exude serum and form a thin pad of fibrin, platelets, and white cells. This compressed clot was then dried for 30 minutes under a heat lamp, forming a dry, tough, but flexible sheet. This sheet was then trimmed to the correct size, sewn in place of the missing eardrum with a few fine resorbable sutures, and packed externally and internally with platelet glue wound sealant. Restoration of a functioning eardrum was seen within six weeks, with resorption and disappearance of the wound sealant of this invention.

The platelet glue wound sealant has been used clinically in the repair of drill (burr) holes in the cranium by admixing plasma-buffy coat concentrate with autologous bone pulp from the drilling process as the bone growth matrix. The platelet glue wound sealant has also been used in conjunction with autologous bone graft (iliac crest), autologous bone chip, cadaver bone, and demineralized bone matrix in the repair of bony defects of the spinal column. The platelet glue wound sealant has also been used in conjunction with autologous bone graft (iliac crest and rib), and in repair of nonunion pathological mandibular fracture. In one case of mandibular repair, a string of antibiotic-impregnated methylmethacrylate beads was included in the wound sealant, imbedded in the soft tissue external to the mandibular bone graft, and encapsulated with additional platelet glue wound sealant. In each case of use of the platelet glue wound sealant in bone defect applications, physician assessment of bone ingrowth was good to excellent. All grafts took, and there was no associated morbidity. Other sources of bone growth matrix such as hydroxyapatite or bone marrow can also be utilized in conjunction with the wound sealant of this invention.

Other applications of the platelet glue wound sealant are apparent to those skilled in the art, including the addition of drugs or other chemicals for localized, controlled application.

Preparation of Anticoagulated Whole Blood

Whole mammalian blood is withdrawn by aseptic or sterile technique from any accessible site. The blood is anticoagulated at the time of withdrawal using a citrate-based anticoagulant. Any citrate-based anticoagulant is suitable. Standard donor blood collection bags contain citrate-based anticoagulants. For example, those made by Terumo Corporation (sold under the tradename TERUFLEX, CPDA-1) contain 63 ml of citrate phosphate dextrose adenine anticoagulant for collection of 450 ml of blood.

Each 63 ml of anticoagulant contains 206 mg citric acid (hydrous) USP, 1.66 g sodium citrate (hydrous) USP, 140 mg monobasic sodium phosphate (hydrous) USP, 1.83 g dextrose (anhydrous) USP and 17.3 g adenine. Anticoagulated blood can be stored for up to five days at room temperature. Preferably, anticoagulated blood is stored for three days, more preferably for 24 hours or less because platelet function begins to diminish after this time, and coagulation factors begin to deteriorate.

Alternatively, anticoagulation can be performed using a dual lumen blood withdrawal set with a citrate-based anticoagulant. Suitable blood withdrawal sets include, for example, Electromedics model BT727BP and Haemonetics model 247. Suitable citrate-based anticoagulants include that from Electromedics (model ELMD-CPD). Each milliliter of the anticoagulant contains 3 mg citric acid (anhydrous) USP, 26.3 mg sodium citrate (hydrous) USP, monobasic sodium phosphate (monohydrate) USP, and 23.2 mg dextrose USP. These blood withdrawal sets facilitate admixture of a citrate anticoagulant simultaneous with drawing of the blood. The amount of anticoagulant is not critical, so long as sufficient anticoagulant to prevent clotting is present. Generally, a ratio of from 10 to 15 ml of the above anticoagulants per 100 ml of withdrawn blood is used. More concentrated anticoagulant solutions can also be used, with appropriate adjustment of the ratio of administration. Blood withdrawn through these sets is conveniently processed at the time of withdrawal.

The blood is preferably collected, anticoagulated, and stored, if desired, at or near room temperature. The remainder of the process is also conveniently performed at or near room temperature. Temperatures below 18° C. or above 21° C. cause faster diminution of platelet function and degradation of desirable coagulation factors.

Preparation of a Plasma-Buffy Coat Mixture

Anticoagulated blood is then subjected to a centrifugal separation process to produce a plasma-buffy coat mixture that contains buffy coat components of the whole blood in plasma and removes red blood cells.

Such dual centrifugation techniques to remove red blood cells are well known, and devices that perform the separation are commercially available. Several brands of equipment are suitable, such as Electromedics AT500, AT750, AT750EF, AT1000, and ELMD500; Dideco-Sorin BT795 series, STAT, and STAT-P; Haemonetics Cell saver 5; and Cobe-Gambro BRAT 2. The equipment is fitted with a standard centrifugal blood fractionation set which is a disposable set that includes a centrifuge bowl, tubing, and collection bags for the process and is available from the equipment manufacturers. Collection bags are connected to the centrifuge bowl outlet line, and blood access lines are attached to the inlet line of the processing set. Suitable sterile disposables for access and collection are also commercially available from, for example, Electromedics (BT727BP or BT727SP), Haemonetics (#247), and Cobe-Gambro.

The machine centrifuge is then, preferably, set to rotate at maximum RPM. Although lower centrifuge speeds can be used, the highest available RPM allows maximal yield with fastest blood flows, thus shortening processing times. In addition, use of the highest centrifuge speed provides the highest red cell packing density and, therefore, the highest yield of platelets and plasma. Typical high speed centrifuge rates are 4800 to 5600 RPM, generating centrifugal forces on the order of 2000 G. Blood flow is then begun at flow rates of from about 50 ml to about 150 ml per minute. Lower flow rates increase the time for the process with no appreciable increase in yield. Higher flow rates do not allow the platelets to separate from the plasma, thus diminishing yield. A flow of about 100 ml/minute in this stage provides a balance of desired effects.

As blood flows through the centrifuge bowl, the denser formed elements are forced to the periphery, while the less dense acellular plasma is forced to the center where it overflows into a collection bag. This process is preferably continued until the centrifuge bowl is nearly filled with formed elements, with only a small central core of clear plasma remaining. The cell pack is typically 70% to 80% formed elements and 20% to 30% plasma.

The blood pump is then stopped and the centrifuge speed reduced to about 2400 RPM. At the now lower forces on the order of about 250 G, the denser red cells and neutrophils remain on the periphery of the centrifuge bowl, while the less dense platelets, monocytes and lymphocytes, the so called "buffy coat", are forced into the central plasma column which becomes cloudy. Lower RPMs may not exert sufficient force to maintain separation between red cells and plasma, which would prevent collection of the buffy coat free of red cells.

The exit line leading to the plasma collection bag is then closed. The exit line leading to another collection bag is opened, and blood flow is reinstituted at from about 25 to about 125 ml/minute. Lower flow rates prolong the process unnecessarily, while higher flow rates diminish the yield of platelets. Blood now entering the centrifuge bowl is again fractionated. At these lower centrifugal forces, the red cells and neutrophils remain in the centrifuge bowl while the plasma fraction continues to exit the bowl, carrying with it most of the platelets, monocytes and lymphocytes into the second collection bag.

Continuing to pump blood into the bowl such that it fills with red cells forces the central plasma column and entrained formed elements into the exit line. Blood flow is continued until red cells first begin to enter the second collection bag, at which point the blood flow is stopped. The volume of blood required to reach this point is inversely proportional to its hematocrit.

The exit line to the platelet bag is then clamped, and the centrifuge stopped. The plasma collection bag is then opened. The blood pump is reversed, and the platelet-poor red cells are directed to a third collection bag. Optionally, some or all of the cell-poor plasma may be recombined with the red cells. The packed red cells, the cell-poor plasma, or the recombined platelet-poor whole blood may be reinfused to the patient immediately, held for later reinfusion, or discarded. A single cycle of filling, fractionating, and emptying requires about 10 to 13 minutes, depending on capacity of the centrifuge bowl, the hematocrit of the withdrawn blood, and the flow rates chosen. The process may be repeated to provide greater volumes of blood component fractions as desired.

Volume yield of the various fractions is dependent on the same parameters that affect processing time. Typically, a 125 ml centrifuge bowl yields about 125 ml of packed red cells, about 100 to 350 ml of cell-poor plasma, and about 25 to 60 ml of buffy coat, depending on the hematocrit of the blood being processed. Larger centrifuge bowls yield proportionately larger volumes. Successively larger volumes of blood withdrawn place a greater stress on the donor, and may dictate the size of centrifuge bowl used and the rate or total volume of processing.

Yield of platelets in the buffy coat is similarly dependent on the parameters that affect cycle time and volume yield, as well as by platelet count in the withdrawn blood and the relative densities of the constituent formed elements. The range of yield is from about 50% to about 80% of platelets entering the bowl, with about 60% to about 70% being the norm. Platelet concentrations in this buffy coat fraction range from about 350,000,000 to about 800,000,000 per ml, with the norm being about 500,000,000 to about 650,000,000 per ml. Fibrinogen level is at or below donor blood value.

Once processed, the plasma buffy coat mixture can be held at room temperature for periods of up to 5 days in qualified platelet storage containers, but the platelets are most functional if utilized within 36 hours of being drawn. Platelets require continuous agitation if held for more than 24 hours from the time of being drawn.

Preparation of a Plasma-Buffy Coat Concentrate

Water is removed from the plasma-buffy coat mixture to prepare a plasma-buffy coat concentrate. This step is conveniently performed using a conventional hemoconcentrator.

A sterile assemblage of commonly available blood bag spikes, stopcocks and tubing is constructed such that the collection bag containing the plasma-buffy coat mixture is connected to a three way stopcock. A fluid transfer set with female luer lock (Codon Medlon Inc., Cat. No. B310), comprising a small diameter PVC tubing fitted with a ratchet clamp and attached at one end to a blood spike and at the other end to a female luer lock, is connected to the buffy coat plasma mixture collection bag by means of the blood spike. A three-way stopcock (commercially available from a number of sources including Medex, Inc.) is attached to the transfer set luer lock fitting. A 60 cc syringe (commercially available from a number of sources including Pharmaseal Inc.) is attached to an arm of the stopcock. The third stopcock arm is fitted with a male luer lock to ¼" tubing adapter (commercially available from sources such as Minntech Corp.), which in turn is fitted with a piece of ¼" PVC tubing (about 2 to about 3 cm in length).

Hemoconcentrators are commercially available from a number of sources including Minntech Corp., Amicon Corp., and others. A preferred hemoconcentrator is described in Applicant's copending application (Ser. No. 08/481,239 filed Jun. 6, 1995 entitled "Device and Method for Concentrating Plasma" [Attorney Docket M-3332 US]) which is incorporated by reference herein in its entirety. The hemoconcentrator is then connected at its inlet to the ¼" tubing. The outlet of the hemoconcentrator is also fitted with a piece of ¼" PVC tubing (about 2 to about 3 cm in length), which serves as the attachment site for the inlet coupler of a blood transfer bag (commercially available from Terumo Corporation and other sources). The plasma-buffy coat mixture can then be aspirated into the syringe. By adjusting the stopcock, the flow path between syringe and the hemoconcentrator is opened. A vacuum at about −400 torr is then applied to the discharge port of the hemoconcentrator, and the plunger of the syringe compressed to force the plasma-buffy coat mixture through the blood path of the hemoconcentrator at 20 to 35 ml/min. Vacuum of from about −100 to about −400 torr can be employed to draw water from the plasma-buffy coat mixture to form a plasma-buffy coat concentrate, with the flow rate of the mixture adjusted inversely in proportion. Once all of the plasma-buffy coat mixture enters the hemoconcentrator, the vacuum is disconnected. The empty syringe is replaced by a syringe full of a physiologic solution that is substantially free from ionized calcium. Physiologic saline, citrated plasma, phosphate buffered saline, and salt-poor albumin are suitable. A 20 cc syringe is conveniently used. The physiologic solution is infused into the hemoconcentrator to flush residual platelets and plasma-buffy coat concentrate from the hemoconcentrator into a receiving transfer bag.

The time requirement for withdrawing water from the plasma-buffy coat mixture to produce a plasma-buffy coat concentrate varies depending on flow rate and the volume processed. The final volume of the plasma-buffy coat concentrate varies as a function of the ratio of flow rate to vacuum level. Ideally, the volume of the plasma-buffy coat mixture is reduced by about 50% to about 66%. Reductions of about 25% to about 50% are suitable but not preferred. Reductions of greater than about 70% risk creating a liquid of such high viscosity that it will be difficult or impossible for flow to occur.

This hemoconcentration step in the process is most conveniently carried out at room temperature.

The plasma-buffy coat concentrate is a viscous, tawny, amber-colored liquid. Platelet counts range from about 1,000,000,000 to about 2,500,000,000 per ml and greater, a 9- to 12-fold increase from the concentration in the drawn blood. White cell counts are from about 30,000,000 to about 60,000,000 per ml, 6 to 9 times donor levels, with a differential of about 60% to about 70% lymphocytes, about 15% to about 25% monocytes, and about 5–25% neutrophils. Other white blood cells, e.g., basophils and eosinophils are substantially absent. In particular, typically, basophils and eosinophils are not present in detectable amounts. Lymphocyte content is increased by about 12- to about 15-fold, and monocytes are increased by about 20 to about 25 times that of the starting blood. Plasma protein levels are from about 12 to about 20 gm/dl. Fibrinogen levels are similarly at about a 2-fold to a 3-fold increase over donor blood values, as are other coagulation proteins. Electrolyte levels are substantially unchanged from drawn blood values, since electrolytes are carried through the hemoconcentrator membrane along with water and other small molecules.

The pore size, or sieving coefficient, of the hemoconcentrator membrane is chosen to retain proteins and other desirable blood constituents, including any contents of the platelets which may be exuded into the plasma during hemoconcentration. Ideally, the pore size or sieving coefficient is a 100% cutoff at 45,000 Daltons, meaning that molecules larger than 45,000 Daltons will be retained in the plasma-buffy coat concentrate.

Once prepared, the plasma-buffy coat concentrate can be used immediately, or can be stored, preferably at room temperature for best preservation of platelet function. Efficacy begins to deteriorate after about 36 hours from the time the blood was initially drawn, and by 5 days at room temperature should be discarded.

Platelet concentrations of about 1,000,000,000 per ml are needed to provide clinically significant acceleration of wound healing when the plasma-buffy coat concentrate is used as a wound healant, and for clinically discernable increases in adhesiveness when used as a wound sealant. If a platelet count is done on the plasma-buffy coat mixture prior to hemoconcentration, and the count is found to be greater than about 500,000,000 per ml, then platelet-poor plasma can be combined with the plasma-buffy coat mixture up to a volume that brings the platelet count to about 500,000,000 per ml. Plasma and plasma-buffy coat mixture can be combined prior to hemoconcentration. Alternatively, the plasma-buffy coat mixture is hemoconcentrated first and the aliquant of plasma second, chasing residual buffy coat contents from the hemoconcentrator. By either method, a larger volume of plasma-buffy coat concentrate can be made without diminution of clinical effectiveness.

In an embodiment for processing large volumes of blood to prepare the wound sealant, the method was performed as follows. The procedure can be readily modified by one of skill in the art.

During setup of a centrifuged blood fractionation set (also referred to as a standard autotransfusion processing kit), a ¼" equal "Y" fitting is interposed with two of its arms between the blood pump boot and the centrifuge bowl, using length of ¼" PVC tubing (conveniently about 15 cm) to connect the "Y" to the centrifuge bowl. The third arm of the "Y" is in turn connected to a second length of ¼" PVC tubing (conveniently about 15 cm) attached to the inlet of a hemoconcentrator. The outlet of the hemoconcentrator is attached to a piece of ¼" PVC tubing (about 2 to about 3 cm in length) which is in turn connected to the inlet coupler of a blood transfer bag. The line leading from the "Y" to the hemoconcentrator is clamped.

Processing then proceeds to fractionate the blood into three components; packed red cells, plasma, and plasma-buffy coat mixture. At completion of the fractionation, the packed red cells alone are pumped to the holding bag, being replaced in the centrifuge bowl by sterile air earlier retained in one of the collection bags.

The plasma and plasma-buffy coat mixture collection bags are then spiked with the clamped dual spike lines of the autotransfusion processing kit, usually reserved for wash solutions. The wash line and the fill line of the processing set are then reversed in the clamping fixture of the autotransfusion processing machine, so that a fill command will draw fluid through the wash line. The spike line in the plasma collection bag is unclamped, and the blood pump is engaged at about 50 ml/minute or less to draw plasma from the collection bag through the processing kit lines and into the centrifuge bowl, thus flushing any residual red cells from the tubing set into the centrifuge bowl.

When the tubing is free from red cells, the spike line to the plasma bag is clamped and the spike line to the plasma-buffy coat mixture collection bag is opened, drawing the plasma-buffy coat mixture towards the blood pump with an air bubble separating the plasma-buffy coat mixture from the plasma. As the air bubble reaches the "Y", the line to the hemoconcentrator is unclamped and the line to the centrifuge bowl is clamped shut. Flow now proceeds to the hemoconcentrator, and vacuum at about −400 torr is applied. When the plasma-buffy coat mixture reaches the hemoconcentrator, water is removed and the plasma-buffy coat concentrate emerges into the transfer bag.

When all of the plasma-buffy coat mixture has been emptied from its collection bag, the blood pump is temporarily stopped. The spike line from the plasma-buffy coat mixture collection bag is clamped, removed from the plasma-buffy coat mixture bag, and inserted into the transfer bag containing the buffy coat/plasma concentrate. If the water-removal step did not remove the amount of water desired, the plasma-buffy coat concentrate can be now reprocessed through the hemoconcentrator until a sufficient amount of water is removed. When water removal is complete, the vacuum should be disconnected from the hemoconcentrator. Recovery of residual plasma-buffy coat concentrate from the hemoconcentrator can be accomplished by pumping plasma from the plasma holding bag into the hemoconcentrator in sufficient volume to displace the plasma-buffy coat concentrate into the transfer bag. As described previously, other physiologic solutions can also be used, but are less preferred as such solutions do not contain blood coagulation proteins.

Mixing with a Fibrinogen Activator

Just prior to application to a wound, the plasma-buffy coat concentrate is mixed with a fibrinogen activator. Addition of the fibrinogen activator starts the clotting process, as described in detail below.

Fibrinogen activators are well known and commercially available, and include thrombin and batroxobin. Thrombin is preferred. Thrombin cleaves fibrinogen into fibrin monomer, which in turn crosslinks to form a fibrin mesh. Mixing of a fibrinogen activator with the plasma-buffy coat concentrate is a rapid and effective means of forming an adhesive coagulum. Further, thrombin is a potent activator of platelets, stimulating adhesiveness and initiating the release reaction in which contents of the platelet granules are expelled. Thrombin is commercially available from several sources, including Armour, Park-Davis, and others. At present, commercially available thrombin preparations are of bovine or equine origin. Standard cautions for those with allergies or previous reactions to thrombin should be used.

In contrast to other fibrinogen-based sealant adhesives, the activated plasma-buffy coat concentrate forms a coherent, strong glue on exposure to thrombin alone, without the need for addition of calcium salts. Calcium carried by the platelets has proven sufficient to allow effective fibrin crosslinking. The presence of added ionic calcium in the presence of platelets is generally undesirable, since it allows the platelets to contract and express serum from the coagulum, an undesirable transformation. Therefore, a fibrinogen activator alone in solution is preferred and is unexpectedly effective. However, in applications wherein slow formation of a clot is desirable, calcium alone can be used to produce thrombin from prothrombin present in the plasma-buffy coat concentrate for formation of a clot over a period of several minutes.

To generate a coherent, uniform coagulum, the fibrinogen activator and the plasma-buffy coat concentrate must be uniformly mixed prior to contact with the target tissue surface. This is most easily achieved by putting the fibrinogen activator in solution, then mixing the two liquids. Commercial thrombin preparations are provided in dry form with sterile saline as a diluent to reconstitute the preparation. Other physiologic solutions consistent with preservation of thrombin activity and the components of the plasma-buffy coat concentrate can be used. Coagulation rates are adjusted to be sufficiently slow to allow application of the wound sealant, but fast enough to ensure rapid adhesion and sealing, once applied. In the presence of sufficient fibrinogen to form a clot, the rate of coagulum formation is directly dependent on the fibrinogen activator concentration in the final mixture. At 100 U of thrombin per ml, for example, a coagulum forms in about 3 to about 5 seconds; at 50 U/ml the rate is about 15 to about 20 seconds, and at 10 U/ml the clot forms in about 60 to about 120 seconds. Thus, the need for faster or slower setting times (up to about one to two minutes) of a particular application can be met by adjusting the fibrinogen activator concentration.

Temperature also affects the rate of clot formation. The application of small quantities, that is, a few milliliters at a time in a thin layer, allows the target tissue to provide sufficient heat to maximally accelerate clot formation, with no need to warm the components above room temperature prior to mixing. Higher temperatures, up to 42° C., can be employed, although such temperatures provide no benefit. Lower temperatures can be used to prolong clotting time, if desired.

Volume ratios of the two liquids are important in determining the strength, adhesiveness, and platelet content of the wound sealant. Minimizing dilution of the fibrinogen and platelets by the fibrinogen activator solution maximizes these concentrations. Although plasma-buffy coat concentrate to fibrinogen activator solution volume ratios of about 5:1 have been successfully employed, the incidence of unsatisfactory results is greater than with higher ratios. Ratios of from about 10:1 to about 12:1 are reliably effective. Higher ratios make thorough mixing of the two solutions more difficult and less reliable.

To achieve the degree of mixing uniformity desirable, two methods have been employed. Both methods are preferably performed at room temperature. In a single syringe method, about 10 to about 12 ml of plasma-buffy coat concentrate are aspirated into a syringe, along with about 1 or 2 ml of air to facilitate mixing. One ml of fibrinogen activator solution is then aspirated, and the syringe is tilted about three times over about 180 degrees in the vertical plane, allowing an air bubble to traverse the length of the syringe and thus repeatedly mix the two solutions.

Alternatively, the two solutions can also be mixed in a small cup or container, using a rod, spatula, or other suitable instrument to rapidly stir them together. Some commercially available mixing devices, such as dual fluid irrigation systems (available from Research Medical and Hemaedics) have been tried but found unsuitable. Such devices are designed for a volume mixing ratio of 1:1, which causes undesirable dilution, and are not easily adaptable to higher volume ratios; and, the frequency of coagulation in the Hemaedics device with resultant plugging was excessive. Application of the wound sealant needs to occur during gelation for maximal adhesion to tissue surfaces. With the syringe method, the wound sealant can be ejected directly on the desired site, using a cannula, catheter, endoscope, or other suitable tube or nozzle as the needs of the situation require. A preferred applicator is described in Applicant's copending application (Ser. No. 08/472,941 filed Jun. 6, 1995 entitled "Wound Sealant Preparation and Application Device and Method" which is incorporated herein by reference in its entirety. The wound sealant is most effective if applied in a thin layer, with additional layers as required for additional strength.

The coagulating wound sealant can be poured from a cup over the desired site while still liquid, or trowelled on with a spatula or similar tool. In any case, a relatively dry site provides the best opportunity for effectiveness. Holding an absorbent sponge or pad on the intended site until the moment of application of the wound sealant is of great benefit.

Blood Processing Kits

The present invention also includes a kit for processing blood to form a plasma-buffy coat concentrate. The kit includes a centrifugal blood fractionation set and a hemoconcentrator. As described previously, a centrifugal blood fractionation set includes a centrifuge bowl, tubing, and collection bags for removing red blood cells in a dual centrifugation technique. Preferably, the components of the kit are sterile and disposable. In another embodiment, the kit also includes blood bag spikes, stopcocks, and tubing for preparing the plasma-buffy coat concentrate.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below, but should not be construed to limit the invention. All literature citations herein are expressly incorporated by reference.

EXAMPLE 1

In an exemplary preparation and use of the wound sealant of this invention, a 57 year old obese diabetic woman presented six weeks post a multi-level vertebral laminectomy, with an unhealed wound and a persistent, large cerebrospinal fluid (CSF) leak of indeterminate origin. Three revision operations had failed to identify the site of the leak, and attempts to seal the leak with a blood patch, collagen foam, transplanted fat pads, compression, and bed rest had all failed. Systemic and topical lavage antibiotic treatments, repeat tissue debridement, wet and dry packs, and placement of drains had failed to address the unhealed wound, which was now 50% larger than the original surgical incision.

After induction of anesthesia for her fourth procedure, a unit of her own blood was withdrawn in sterile fashion from her antecubital vein. The blood was collected in a standard sterile blood donor set, using CPDA-1 anticoagulant (Terumo Corporation). Analysis of the collected blood showed a hematocrit of 34% and a platelet count of 224,000,000. White cell count was 7,200 per ml with differential analysis showing 63% neutrophils, 29% lymphocytes, 5% monocytes, 2.2% eosinophil, and 0.8% basophil. Fibrinogen was assayed at 2.85 mg/ml.

The collected blood was connected to a sterile disposable blood processing set manufactured by Electromedics Inc., which was in turn mounted on an ELMD500 Autotransfusion System also by Electromedics. The centrifuge bowl (125 ml) was set to rotate at 5600 RPM, generating forces within the blood path in the bowl on the order of 2000 G. The blood was then pumped into the bowl at 50 ml per minute.

When the bowl was nearly full of packed cells with only a small central core of clear plasma remaining, the blood pump was stopped and the centrifuge speed reduced to 2400 RPM. The exit line leading to the plasma collection bag was closed, the exit line leading to another collection bag was opened, and blood flow was reinstituted at 50 ml/min. The blood now entering the centrifuge bowl was again fractionated, but at the lower centrifugal force, the red cells and neutrophils remained in the centrifuge bowl.

The plasma fraction continued to exit the bowl, carrying with it most of the platelets, monocytes, and lymphocytes into the second collection bag to produce a plasma-buffy coat mixture. Blood continued to be pumped into the bowl such that it filled with red cells, forcing the central plasma column and entrained formed elements into the exit line. Flow continued until the point where red cells first began to enter the second collection bag. At that point the blood flow was stopped; the exit line to the bag containing the plasma-buffy coat mixture was clamped; and the centrifuge was stopped.

The plasma collection bag containing the plasma-buffy coat mixture was then opened. The blood pump was reversed. By means of clamps, the platelet-poor red cells and plasma were directed to a third collection bag. The process was repeated until all the whole blood that had been collected had been processed. The reconstituted platelet-depleted whole blood was then reinfused to the patient.

Elapsed processing time for the dual speed centrifugation fractionation process was 18 minutes. The yield of the plasma-buffy coat mixture was 45 ml, with a platelet count of 628,000,000 per milliliter and a white cell count of 14,300 per milliliter. Leukocyte differential analysis showed lymphocytes at 72%, monocytes at 21%, neutrophils at 6%, other types at less than 1%. Hematocrit was 0.3. Fibrinogen was 2.80 mg/ml. This plasma-buffy coat mixture was then further processed.

A sterile assemblage of commonly available blood bag spikes, stopcocks and tubing was constructed such that the platelet bag was connected to a three way stopcock. A second port of the stopcock led to a 60 cc syringe, and the third leg led to a 0.25 square meter surface area hemoconcentrator manufactured by Minntech Inc., the outlet of which was in turn connected to a Terumo Corporation sterile blood transfer bag. The plasma-buffy coat mixture was then aspirated into the 60 cc syringe. By adjusting the attached stopcock, the flow path between syringe and hemoconcentrator was opened. A vacuum of -400 torr was applied to the discharge port of the hemoconcentrator, and the plunger of the 60 cc syringe was compressed to force the plasma through the blood path of the hemoconcentrator over about two minutes to produce a plasma-buffy coat concentrate.

The vacuum was immediately disconnected, and the empty 60 cc syringe was replaced by a 20 cc syringe full of normal saline. The saline was immediately infused into the hemoconcentrator to flush residual plasma-buffy coat concentrate from the device into the receiving transfer bag to form the final plasma-buffy coat concentrate. This process required only one minute to complete.

The plasma-buffy coat concentrate was 18 ml of a viscous, tawny amber colored liquid. Analysis showed a platelet count of 1,532,000,000 and a white cell count of 35,600 per milliliter, with an unchanged differential. Fibrinogen was measured at 6.68 mg/ml, and hematocrit was measured at 0.5%.

This plasma-buffy coat concentrate was aspirated into a 20 cc syringe and transferred in sterile fashion into a medicine cup on the sterile surgical field. Nine ml of the plasma-buffy coat concentrate was aspirated into each of two 12 cc syringes, along with 2 ml of air, which were then affixed with 14 gauge plastic cannulae and set aside. Additionally, 5,000 units of bovine Thrombin USP (sold under the tradename THOMBOSTAT by Parke-Davis), was dissolved in 5 ml of accompanying sterile saline, for a concentration of 1,000 U per milliliter.

When the surgeon had finished debridement and other treatment of the wound and had exposed an apparent site of CSF leakage, the surgical assistant retrieved one of the 12 cc syringes and aspirated one ml of thrombin solution. By rocking the syringe 180 degrees in the vertical, the air bubble caused rapid mixing of the two liquids. The syringe was passed to the surgeon who immediately expelled the contents directly on the desired tissue site. A whitish coagulum formed within five seconds, covering the suspected CSF leak site. A small autologous fascia patch was sewn over the coagulum for additional stability. The contents of the second plasma-buffy coat concentrate syringe were similarly treated and applied in a thin layer over the remaining wound surfaces. Conventional closure of the wound was accomplished, with placing of a small silicone sump drain and a dry skin dressing.

The patient was mobilized to a sitting position 48 hours post-op, with no apparent CSF leak. Wound drainage was less than 10 cc, and the drain was pulled at 72 hours post-op. The wound showed conventional healing with minimal redness of the surrounding tissue and no wound exudate. The patient was discharged uneventfully at four days post-op. At three months follow up, the patient showed a fully healed wound with no evidence of a CSF leak.

EXAMPLE 2

In another exemplary use of the platelet glue wound sealant of this invention, a 72 year old, 58 Kg woman presented for open heart surgery and cardiopulmonary bypass with replacement of her ten year old prosthetic mitral valve and triple coronary artery bypass grafting. Studies and experience have shown that this type of patient carries substantial risk factors for blood loss and transfusion requirement, including advanced age, small body mass, reoperation, and combined cardiac surgical procedures. This patient would be anticipated to produce 1,500 ml of post-operative chest wound drainage or more, and to be at a 50% or greater risk for requiring transfusion with a 30% or greater risk of multiple transfusions.

After induction of anesthesia, blood was withdrawn from a catheter placed in the right internal jugular vein via an Electromedics dual lumen line and connected to the inlet line of the blood processing disposable set. Citrate anticoagulant solution, also made by Electromedics (3 mg citric acid (anhydrous) USP, 26.3 mg sodium citrate (hydrous) USP, monobasic sodium phosphate (monohydrate) USP, and 23.2 mg dextrose USP), was connected to the second lumen and thereby admixed with the patient's blood as it was withdrawn, at a ratio of 15 ml citrate solution to 100 ml patient blood.

An inlet line of the blood processing disposable set, manufactured by Sorin, Inc., was routed to a blood pump on the autotransfusion system (Dideco Inc., Model BT795AT), which controlled the flow of blood from the patient. For the first stage of separation, the centrifuge speed was set at 4800 RPM, and blood flow was begun at 100 ml/minute. The centrifuge bowl (225 ml capacity) was filled as described in Example 1, before generating a cell-poor plasma fraction. As in Example 1, the blood flow was interrupted, the centrifuge speed reduced to 2400 RPM, and blood flow resumed at 50 ml/minute to produce a buffy coat fraction of 68 ml volume.

After withdrawal into a syringe, the fractionation process was continued to generate a store of autologous plasma-buffy coat mixture and plasma for reinfusion after discontinuation of cardiopulmonary bypass, while red cells were returned to the patient before bypass commenced.

The plasma-buffy coat mixture was concentrated as in Example 1, using in this case a hemoconcentrator from Amicon Inc. The plasma-buffy coat concentrate volume produced was 26 ml. Analysis of the blood in its various process steps (as drawn from the Patient, in the plasma-buffy coat Mixture, and in the plasma-buffy coat Concentrate) was as follows:

| Analyte | Patient | Mixture | |
|---|---|---|---|
| Concentrate Hct (%) | 36 | 0.4 | 0.8 |
| Fibrinogen (mg/ml) | 2.12 | 2.19 | 5.11 |
| Platelets ($10^6$/ml) | 186 | 568 | 1,370 |
| Leukocytes ($10^6$/ml) | 8.2 | 16.6 | 41 |
| Differential (%) | | | |
| neutrophils | 61 | 7 | 6 |
| lymphocytes | 27 | 59 | 60 |
| monocytes | 8 | 34 | 34 |
| eosinophils | 3 | — | — |
| basophils | 1 | — | — |

At the completion of cardiopulmonary bypass, the remaining sequestered plasma and plasma-buffy coat concentrate not used in the wound sealant were administered intravenously. The plasma-buffy coat concentrate was passed to the sterile field as described in Example 1, along with 10,000 Units of Thrombin USP (Armour, Inc) dissolved in 10 cc of normal saline. The plasma-buffy coat concentrate was aspirated equally into two 20 cc syringes, and the thrombin solution equally into two 5 cc syringes. Each syringe was fitted with a spray nozzle tip from Hemaedics, Inc.

When application was desired, the surgeon held a plasma-buffy coat concentrate syringe in one hand and a thrombin syringe in the other, expelling the contents of each onto the tissue surfaces in an overlapping pattern of sprays. The contents of all four syringes were expelled, covering the mediastinum, the resected adhesions covering the surface of the heart, the cardiotomy sites, the root of the aorta, the inner walls of the chest, and the cut sternum. Drains were placed and the wounds were closed by standard protocol.

Total post-operative mediastinal chest drainage was 358 ml. and the patient was off the ventilator and discharged from ICU to a stepdown unit the morning after surgery. Post-op course was uneventful and the patient was discharged on day 6 without the need for any allogeneic blood.

EXAMPLE 3

The effect on gelation time of re-activation of endogenous thrombin in the plasma-buffy coat concentrate was studied. The following table illustrates the effect of various ratios of 10% calcium citrate to plasma-buffy coat concentrate on gelation time at 22° C. In this study, no exogenous fibrinogen activator was used.

| Ratio of Volume of 10% CaCl$_2$ to Plasma-Buffy Coat Concentrate | Gelation Time at 22° C. |
| --- | --- |
| 1:5 | 30 |
| 1:10 | 12 |
| 1:11 | 11 |
| 1:12 | 11 |

A study was performed to determine the effect of temperature on gelation time. In the study, one part of 10% CaCl$_2$ solution was mixed with 11.5 parts of plasma-buffy coat concentrate.

| Temperature | Gelation Time |
| --- | --- |
| 22° C. | 11 minutes |
| 32° C. | 5 minutes |
| 37° C. | 2.5–3 minutes |

As can be seen from this study, gelation times of from two to thirty minutes can be produced if desired by addition of ionic calcium to the plasma-buffy coat concentrate.

EXAMPLE 4

This example describes studies using a plasma-buffy coat concentrate and ground dry bone, wherein clot formation was produced by exposure to calcium chloride. The study was performed using a plasma-buffy coat concentrate produced from bovine blood and having a fibrinogen concentration of 570 mg/dl and a platelet count of 1,200,000,000/ml.

Six different compositions were studied. The bovine plasma-buffy coat concentrate was used alone or combined with either 10% CaCl$_2$ or a commercial preparation of ground dry bone meal. The results of the study are illustrated in the following table. In the table, the ratio of the plasma-buffy coat concentrate to CaCl$_2$ is in ml concentrate:ml CaCl$_2$, and the ratio of the concentrate to bone meal is in ml concentrate:cc bone meal. No thrombin was added to any of the compositions. All compositions were allowed to stand covered at room temperature (22° C.).

| Sample | Ratio CaCl$_2$ | Ratio Bone Meal | Results |
| --- | --- | --- | --- |
| 1 | NA* | NA | Remained liquid for four hours until the study was terminated |
| 2 | 1:5 | NA | Gelled firmly in 30 minutes |
| 3 | 1:10 | NA | Gelled firmly in 12 minutes |
| 4 | NA | 2.5:0.1 | Gelled firmly in 90 minutes |
| 5 | NA | 2.5:2.5 | Semi-solid, but soft and formable immediately; Gelled firmly in 45 minutes |
| 6 | NA | 2.5:5.0 | Firmly solid, but formable immediately; Gelled firmly in 20 minutes |

*Not Applicable; indicates that CaCl$_2$ or bone meal was not present

By comparing Samples (2) and (3) to (1), this study determined that calcium ions alone are sufficient to coagulate the plasma-buffy coat concentrate, albeit slowly, when present in excess of the quantity needed to neutralize all free citrate. Samples (4), (5), and (6) demonstrated that dry ground bone, predominantly hydroxyapatite, can have the same effect. This may be due to chelation of the citrate by the solid bone, thus freeing calcium ions for clot formation; or, by dissolving calcium ions from the bone matrix to provide enough free ionized calcium to allow coagulation to occur; or a combination of both. Sample (4) also demonstrated that only a small quantity of bone meal is required to coagulate a much larger volume of plasma-buffy coat concentrate. Samples (5) and (6) showed that by admixing increasing quantities of bone meal relative to plasma-buffy coat concentrate volume, firmer and firmer gels can be produced. These gels develop good working characteristics immediately upon mixing, which would allow the formation of any desired shape or configuration. On standing, these mixtures attain increased firmness and strength.

An advantage of use of calcium over other techniques for initiating clotting is the absence of need for exogenous thrombin, the source of some number of patient complications. Another advantage illustrated by Samples (4), (5), and (6) is that the composition can be molded to fit virtually any desired configuration, and in Samples (5) and (6) especially, the formation of a firm paste eliminates the tendency of the sealant to run and escape the intended application site prior to clot formation. At the same time, the presence of the plasma-buffy coat concentrate transforms the bone meal from a fine particulate nature into a workable paste which facilitates application to any recipient site. Another advantage is the presence of tissue growth stimulating substances from the platelets, which have shown accelerated and completed wound healing when used with autologous bone pulp. The same benefit may be conferred on hydroxyapatite or another exogenous source of bone growth matrix, without need for thrombin exposure.

This study illustrates the benefits of use of the platelet glue wound sealant for bone repair in humans and in similar veterinary applications.

What is claimed is:

1. A plasma-buffy coat concentrate comprising:
   a. plasma;
   b. platelets at a concentration of at least $1.0 \times 10^9$ cells/ml;
   c. fibrinogen at concentration of at least 5 mg/ml; and
   d. white cells at a concentration of at least $3.0 \times 10^7$ cells/ml.

2. The plasma-buffy coat concentrate of claim 1 wherein platelet concentration is from about $1.0 \times 10^9$ cells/ml to about $2.5 \times 10^9$ cells/ml.

3. The plasma-buffy coat concentrate of claim 1 wherein the fibrinogen concentration is from about 5 to about 15 mg/ml.

4. The plasma-buffy coat concentrate of claim 1 wherein white cell concentration is from about $3.0 \times 10^7$ cells/ml to about $6.0 \times 10^7$ cells/ml.

5. The plasma-buffy coat concentrate of claim 4 wherein the white cells comprise about 60 to about 70% lymphocytes, about 15 to about 25% monocytes, and about 5 to about 25% neutrophils.

6. A wound sealant comprising:

a. plasma;

b. platelets at a concentration of at least $1.0 \times 10^9$ cells/ml;

c. fibrinogen at concentration of at least 5 mg/ml;

d. white cells at a concentration of at least $3.0 \times 10^7$ cells/ml; and e. a fibrinogen activator in a concentration sufficient to initiate clot formation.

7. The wound sealant of claim 6 wherein the fibrinogen activator is selected from the group consisting of thrombin and batroxobin.

8. The wound sealant of claim 7 wherein the fibrinogen activator is thrombin.

9. The wound sealant of claim 8 wherein the thrombin is produced from prothrombin present in the plasma component of the wound sealant.

10. A method for processing blood comprising:

a. centrifugally fractionating anticoagulated blood to remove red blood cells and produce a plasma-buffy coat mixture; and b. hemoconcentrating the plasma-buffy coat mixture to remove water from the mixture to produce a plasma-buffy coat concentrate.

11. The method of claim 10 further comprising mixing the plasma-buffy coat concentrate with a fibrinogen activator to produce a wound sealant.

12. The method of claim 11 further comprising applying the wound sealant to a wound.

13. The method of claim 10 wherein the blood is processed peri-operatively.

14. The method of claim 10 wherein the volume of water removed from the plasma in about (b) is between about 50 and about 75 percent of the original plasma volume.

15. The method of claim 10 wherein the leukocyte concentration of the plasma-buffy coat concentrate is at least five times the leukocyte concentration of the blood.

16. The method of claim 15 wherein the lymphocyte, monocyte, and platelet concentrations of the plasma-buffy coat concentrate are at least ten times the respective concentrations of the blood.

17. A method of promoting wound sealing comprising:

a. centrifugally fractionating anticoagulated blood to remove red blood cells and produce a plasma-buffy coat mixture;

b. hemoconcentrating the plasma-buffy coat mixture to remove water from the mixture to produce a plasma-buffy coat concentrate;

c. mixing the plasma-buffy coat concentrate with a fibrinogen activator to produce a wound sealant; and d. applying the wound sealant to a damaged tissue.

18. The method of claim 17 wherein the blood and the tissue are human.

19. The method of claim 17 wherein the blood and the tissue are from the same animal.

* * * * *

UNITED STATES PATENT AND TRADEMARK OFFICE
CERTIFICATE OF CORRECTION

PATENT NO. : 5,733,545

DATED : March 31, 1998

INVENTOR(S) : Andrew G. Hood, III

It is certified that error appears in the above-identified patent and that said Letters Patent is hereby corrected as shown below:

At Column 3, line 32 please change "$1.30 \times 10^9$" to --$1.0 \times 10^9$--

Signed and Sealed this

Fifteenth Day of August, 2000

Attest:

Q. TODD DICKINSON

Attesting Officer     Director of Patents and Trademarks